(12) United States Patent
Schmidt

(10) Patent No.: US 7,125,851 B1
(45) Date of Patent: *Oct. 24, 2006

(54) ENDOPROSTHESIS WITH LONG-TERM STABILITY

(76) Inventor: Karlheinz Schmidt, Äussere Weiler Strasse 12, D-72810 Gomaringen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/958,098

(22) PCT Filed: Apr. 20, 2000

(86) PCT No.: PCT/DE00/01279

§ 371 (c)(1),
(2), (4) Date: Dec. 6, 2001

(87) PCT Pub. No.: WO00/62834

PCT Pub. Date: Oct. 26, 2000

(30) Foreign Application Priority Data

Apr. 20, 1999 (DE) .................. 199 17 696

(51) Int. Cl.
*A61K 38/17* (2006.01)
*A61K 38/16* (2006.01)

(52) U.S. Cl. .............. 514/22; 514/12; 514/21

(58) Field of Classification Search ............ 423/201.1, 423/202.1; 623/1.1, 1.4, 1.41, 1.44, 1.46, 623/1.47, 1.48, 1.49, 11.11, 16.11, 17.18, 623/17.19, 23.63, 23.73; 624/23.57; 514/12, 514/21, 22

See application file for complete search history.

(56) References Cited

U.S. PATENT DOCUMENTS

| | | | |
|---|---|---|---|
| 4,330,891 A | 5/1982 | Branemark et al. | |
| 4,919,666 A | 4/1990 | Buchhorn et al. | ............ 623/16 |
| 5,108,436 A * | 4/1992 | Chu et al. | ............ 424/422 |
| 5,207,710 A * | 5/1993 | Chu et al. | ............ 128/898 |
| 5,456,717 A | 10/1995 | Zweymuller et al. | ........... 623/8 |
| 5,545,208 A | 8/1996 | Wolff et al. | ............ 623/1 |
| 5,824,651 A | 10/1998 | Nanci et al. | ............ 514/21 |
| 5,876,454 A * | 3/1999 | Nanci et al. | ............ 424/423 |
| 5,932,207 A * | 8/1999 | Schmidt | ............ 424/85.1 |

FOREIGN PATENT DOCUMENTS

| | | | |
|---|---|---|---|
| EP | A-0 381 898 | 4/1990 | ............ 623/16.11 |
| EP | 0 366 029 | 5/1990 | ............ 424/523 |
| GB | A-2 164 042 | 3/1988 | ............ 623/1.47 |
| JP | A-1 151461 | 6/1989 | ............ 623/16.11 |
| JP | A-7 8547 | 1/1995 | ............ 424/523 |
| RU | 2 025 132 | 12/1994 | |
| RU | 2 062 622 | 6/1996 | |
| SU | 1 818 091 | 5/1993 | |
| WO | WO 91/06324 | 5/1991 | ............ 424/85.1 |
| WO | WO 93/20857 | 10/1993 | ............ 424/523 |

OTHER PUBLICATIONS

CD Daly, GR Campbell, PJ Walker, JH Campbell, In vivo engineering of blood vessels, 2004, Front. Blosci., 9, 1915-1924.*
K. Anselme, Osteoblast adhesion on biomaterials, Biomaterials 21, 2000 pp. 667-681.

* cited by examiner

*Primary Examiner*—Bruce R. Campell
*Assistant Examiner*—Andrew D. Kosar
(74) *Attorney, Agent, or Firm*—Blank Rome LLP

(57) ABSTRACT

The invention relates to the use of an active substance complex for creating biological parts, in particular organs for living organisms, with the following components which differ from one another and are specifically adapted to the respective biological part which is to be created, namely at least one structural component based on extracellular material specifically adapted to the cells of the respective biological part which is to be created, at least one recruiting component, at least one adhesion component, and at least one growth and/or maturation component for producing an endoprosthesis implant.

Figure 1:
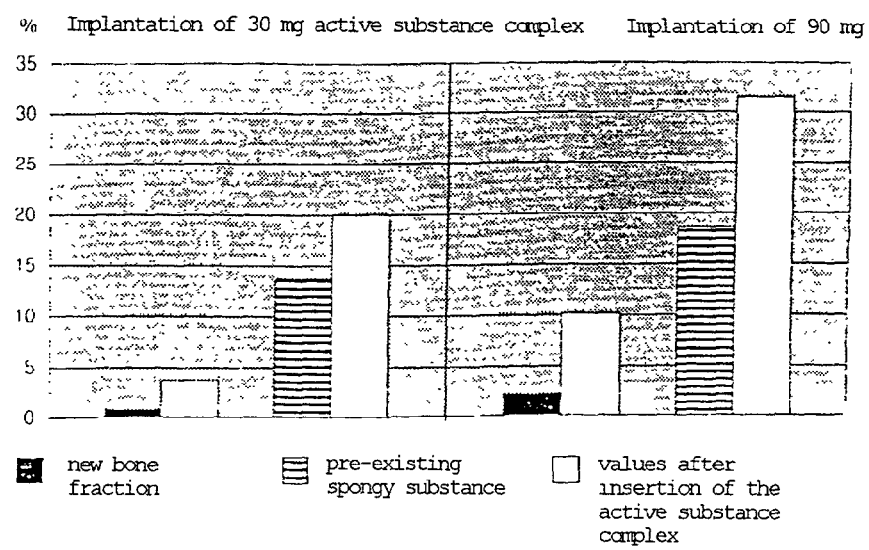

The outer surface (I) of the endoprosthesis is coated at least partially with the active substance complex. In addition, the endoprosthesis has at least one cavity (II) which is filled with the active substance complex.

In order to reduce the amount of active substance complex needed for filling the at least one cavity (II), the active substance complex can additionally be applied to a further support material such as collagen or a suitable polymer.

13 Claims, 3 Drawing Sheets

- new bone fraction
- pre-existing spongy substance
- values after insertion of the active substance complex

- collagen
- collagen* CaA
- collagen *OP
- collagen *CaA+OP

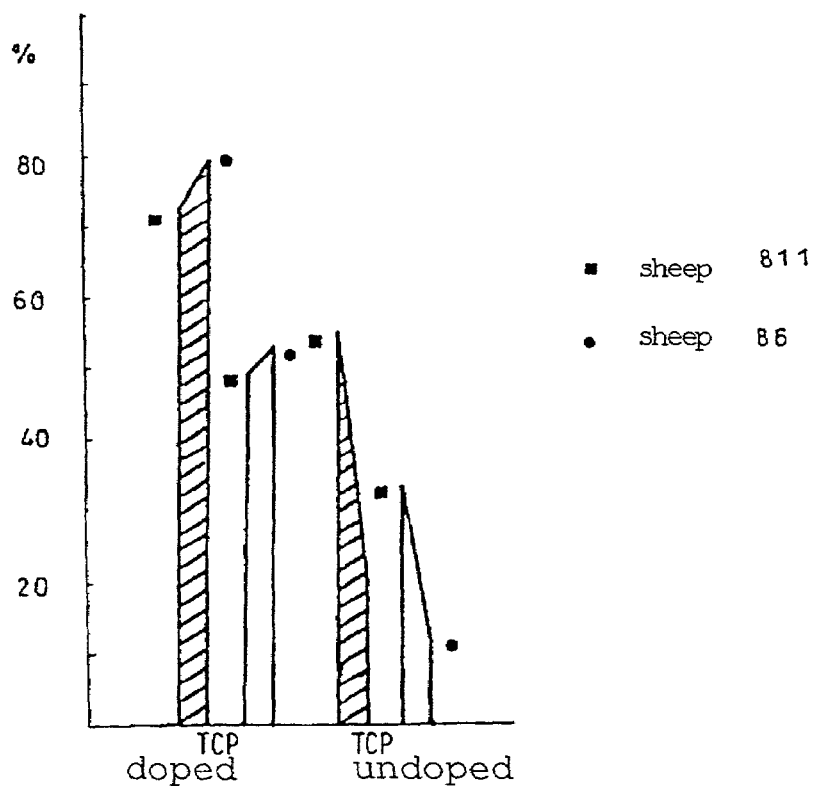

ENDOPROSTHESIS WITH LONG-TERM STABILITY

The invention relates to the use of an active substance complex for creating biological parts, in particular organs for living organisms, with the following components which differ from one another and are specifically adapted to the respective biological part which is to be created, namely at least one structural component based on extracellular material specifically adapted to the cells of the respective biological part which is to be created, at least one recruiting component, at least one adhesion component, and at least one growth and/or maturation component.

An active substance complex for creating biological parts, in particular organs for living organisms, with said components is already known in the prior art.

This object is attained by a complex active ingredient comprising a structure component, at least one recruiting component, at least one adherence component, and at least one growth and/or maturation component, preferably in the form of at least one cytokine.

That known active substance complex has the quality of passing over cells with a reciprocal reaction and inducing them to form a biological part. For this purpose the active substance complex (implant), which can also be performed on an industrial scale, for instance in the framework of series manufacture, is to be produced outside the body of the living organism and then brought into contact with cells which are to form the biological part. This can occur at a suitable site to which the active substance complex is introduced, which can actually be inside the body of the living organism, but can also be outside the body, for instance in a cell culture. In doing this, the active substance complex according to the invention is brought together with an accumulation of vital, function-capable and specific cells at the desired site for formation of the biological part.

As is known, biological parts generally consist of specific cells and extracellular material produced by the cell, but only the cellular portions have their own metabolic activity. Since the active substance complex according to the invention arranges everything for the production of the signals required for the biological part, it is now possible to hold the cells required for this purpose at the site of the active substance complex to the desired geometry, to increase their number and to mature them with a view to the desired functions. Because the active substance complex for the production of biological parts contains the suitable relevant component for any required partial formation step, its production is guaranteed in its entirety.

Furthermore, with use of the active substance complex according to the invention, same-body cells can be used for production of the biological part, so that the known difficulties which arise with the otherwise traditional transplantations are overcome. Especially, transmission of illness is no longer possible, and likewise no long-term immunosuppression with its grave side effects is required, and the individual living organism remains a genetically uniform entity.

Biological parts take up a certain amount of space for their functional performance. Frequently their function is connected with a certain geometry within they fulfill their function. This is also true for the biological parts produced by means of the active substance complex of the present invention. The active substance complex used for production of a biological part fulfills this function with the aid of a structure component which one the one hand exerts the space-retaining function and on the other hand allows the assumption of the existence of a geometric form within which the biological part which is produced fulfills its function.

In one preferred embodiment, the active substance complex of the present invention is primarily a macromolecular three-dimensional matrix, which together with water and salt can be present in the form of a gel of distinct expansion properties. Thus, for instance, proteoglycan gels may form the matrix. A network of fibers, such as, for instance, different types of collagens, or elastin, can also form the structure component. Likewise, combinations of gels with intercalated fibers are suitable composite materials. The structure component for the production of biological parts is manufactured differently for the different intended uses, so that it can be used as a fleece, a gel or a liquid gel, which can be cut, milled, or be plastically deformed or cast.

The structure component is adapted to the requirements of the biological part to be produced, since a certain specificity exists between cellular and the extracellular portions of biological parts. Sources for the production of the structure component are therefore primarily extracellular materials of different tissues or organs. For instance, for the production of skin, or for the production of the structure component, cutaneous proteoglycan and fiber proteins are used; for the production of the spleen, spleen-specific proteoglycans and fibrous proteins are used; for the production of bone, bone-specific proteoglycan and fibrous proteins are used: etc. The structure component can also include metallic, ceramic, vitreous, polymeric or fatty carrier materials, to aid in the modification of the geometric, mechanical, chemical or special properties of the structure component. Thus, the carrier material together with the structure component can be present in solid, porous, membranous, micell, viscous or liquid form according to the requirements, which are determined for the production of the biological part and its subsequent function.

In another preferred embodiment of the active substance complex according to the invention, the material displays its capacity for production of the biological parts essentially only temporarily. In other words, the active substance complex is configured so that it is cyclically controllably decomposable and following the production of the biological part is then no longer even present. The rate of decomposition of the active substance complex can thus be assumed by different transverse cross-linking of the polymeric matrix and/or the addition of (enzyme) inhibitors and/or immunosuppressive and/or inflammation-inhibiting materials. The inhibitors claimed in this writing can be low-molecular compounds which occupy the active center of the decomposing enzyme but they can also be chelating agents, which bind an essential cofactor of the enzyme to themselves, or to neutralizing antibodies. Other types of inhibiting mechanisms are possible.

As inflammation-inhibiting and/or immunosuppressive additives, the following can be used: inhibitors of the phospholipase, such as, for instance, steroids, inhibitors of cyclooxygenase, such as, for instance, indomethacin inhibitors of the lipozygenase, such as, for instance, nordihydroguaiaretic acid, immunosuppressives of the type including cyclosporine and/or of the type including anithymocytene-globulin, etc.

According to this invention, to produce biological parts, living cells of the desired type are to be collected in the region of the structure component. For this purpose the structure component of the active substance complex includes one or more recruiting components with the aid of which the desired cells are stimulated to move in a certain direction. Chemotactica (chemotaxines) are suitable for use as recruiting component(s).

The chemotactica suitable for this use have been described for a number of cells and can be isolated from human, animal, plant or microbial sources of even be produced by chemical synthesis or biotechnical methods. If the structure component projected outside the body of the living organism is introduced with its recruiting component(s) into an organism and/or is brought into contact with target cells outside the organism, it then builds a concentration gradient, in which the target cells are oriented, whereby the relevant recruiting component correlates with the specific identification or recognition structures on the target cells, which are characterized as receptors. For the case wherein the biological part to be produced is composed of a plurality of types of cells, the structure component, corresponding to the number of types of cells, includes a plurality of recruiting components in the form of chemotactica.

The specificity of the relevant recruiting component of the different target cells as well as the amount of chemotactic activity is ascertained by research, wherein the directed migration of the desired cells through defined filter pores is measured under the effect of a certain gradient of the chemotacticum in a chamber. The active ingredient system can be biologically standardized relative to its relevant recruiting component by means of researched techniques of this sort, which is important for the industrial production of the active substance complex.

Peptides for instance such as N-F-met-leu-phe and/or for instance metabolites of arachidonic acid, such as leukotrienes, with the aid of which certain cells can be attracted out of the blood, or phagocytes, will serve as chemotactica. Proteins, such as for instance a protein which attracts mesenchym cells, work chemotactically especially on connective tissue cells.

In addition to the specificity of the recruiting component for the desired target cells and the amount of chemotactic activity, the time duration of the activity during which the chemotactic concentration gradient is built up is also specific and is of considerable length. This kinetic is adapted to the requirements for production of biological parts by the active substance complex according to the invention by means of a controllable liberation of the relevant recruiting component from the structure component. In doing this at this point, the rate of decomposition of the structure component plays a role, as does also the type of connection between the structure component and the relevant recruiting component, dependent for instance on whether it has to do with a covalent or an associative linkage. With covalent linkage, slower synthesis and longer maintenance of the chemotactic gradients is attained than with merely associative linkage made up of ionic forces or hydrogen bridge linkage. The recruiting of the cells for production of the biological part however for the most part occurs more rapidly than the decomposition of the structure component, since the infused cells are quite essential for decomposition of the proteoglycen/collagen material.

For production of the biological parts, following infusion of the cells into the structure component, these cells are in turn to be fixed at the site of the structure component, in order to prevent its emigration into the environment and to guarantee a stable architecture of the biological part which is produced. For this purpose the active substance complex, includes one or more adherence components, by means of which the infused cells can be fixed at the site of the structure component. Thus the adherence components "anchor" themselves on the one hand to the cells being built up on the biological parts and on the other hand to the macromolecular network of the structure component. Adhesins which are known as having a certain anchoring specificity include proteins such as fibronectin or laminin, with the aid of which connective tissue cells or epithelial cells can be anchored to the structure component. Numerous other adherence factors of different specificity can be made available and come into use according to the biological part to be produced with the active substance complex according to the invention. Among others, cell adherence molecules L-CAM and N-CAM belong to this group; the adherence molecules cytotactin, tenas, laminin, fibronectin, collagen types IV, V, VIII, as well as synthetic peptides, and the partial sequences of different adhesions represent the matrix, and transmemebrane protein compounds, such as for instance integrin.

To increase the specificity of attachment of the desired cells to the structure component during production of the biological parts, antibodies inhibiting undesired adherence components can be introduced. The biological activity of the adherence components can be measured in adherence tests of various types (e.g. by means of centrifugal forces, etc.) and thus can be standardized for the entire active substance complex.

Frequently the cells are fixed by suitable adhesions and chemotactically attracted to the area of the structure component for production of the biological part are insufficient in number to constitute the biological part. Also, the mobile cells available in an organism for this process are found for the most part in an insufficiently mature state to fulfill all of the functions of a biological part, wherein they frequently represent precursors or parent cells out of which the function-capable, mature cells of the biological part to be produced must then develop. For this purpose the active substance complex according to the invention has at least one growth and/or maturation component, preferably in the form of one or more cytokines, under the effect of which the number of infused cells is increased and also a maturation of the cells occurs.

Cytokines are materials of distinct chemical structure which are characterized in that they cooperate in reciprocal reaction with cells and influence the splitting and growth of cells as well as their maturation and biosynthesis. Cytokines thus have a hormone-like effect but do not display this quality in the presence of hormones from a distance but rather only in localized areas, which is advantageous in the production of biological parts, since this is a localized process.

A great number of different cytokines of different specificity are known. These can be used to influence cell growth, differentiation and maturation and also to influence the metabolism of the infused cells which are introduced as other components in the active ingredient system according to the invention. The specificity of the cytokines for certain cells is determined by the presence of corresponding receptors on the target cells, whereby the interaction of a cytokine with the receptor triggers the resulting cellular reaction. The receptors on the target cells describes in this case are found in membrane proteins, which pass into reciprocal reaction with the chemotacticum which is being used, link with it and invade the cell. With recycling of the receptors they are again available for linkage with chemotacticum. Analogously, with the receptors for the cytokines being introduced, it has only to do with a different specificity, while with the same reciprocal reaction mechanism. While the linkage of the chemotacticum leads to directed movement of the target cells, the linkage of the cytokines to the corresponding receptor of the target cell results in growth and/or differentiation. Frequently the receptors are not yet characterized molecularly, so that they are known only by their specificity for the relevant ligands (chemotacticum, cytokine, etc.)

Therefore, it is to be taken into account that not infrequently stimulating or inhibiting sequential processes can be triggered at the cells, according to the specificity of the relevant cytokine and target cells. The desired cellular reaction of the cytokine in terms of reciprocal reaction for the production of biological parts is generally connected with a dual signal transmission, so that in an advantageous manner at least two cytokines are used in the active substance complex according to the invention, in order to attain both growth and differentiation. Following interaction with a cytokine, many cells produce more cytokines and release them, whereby the cells themselves can thus be stimulated or inhibited (the so-called autokriner mechanism). Frequently the specificity of the cells for certain cytokines is modified with individual differentiation steps, so that no longer can any interaction occur, or even the reciprocal reactions of a sequential reaction can change over from a stimulating to an inhibiting cellular reaction. The properties of a number of cytokines are known, so that the cytokine effect can likewise be standardized in the active ingredient system.

Some examples of cytokines, which for instance, function in the production of blood, are the factors stimulating colonies, there being, in the production of connective tissue the fibroblasts growth factor, in the production of skin the epidermal growth factor, in the production of cartilage the cartilage-inducing factor, in the production of spleen or lymph nodes the lymphocytes-activating factor as well as spleen peptide, for the production of thymus the T-cells growth factor as well as thymus peptide, for the production of bone the bone growth factor as well as the transforming growth factor, for the production of blood vessels the anglogenesis factor. Furthermore, the following cytokines are also used: interleukins, growth factors similar to insulin, tumor necrosis factor, prostaglandins, leukotrins transforming growth factors, growth factor deriving from thrombocytes, interferons, as well as growth factors deriving from endothelial cells.

Since biological parts are composed most often of a plurality of cell types, combinations can occur. Thus for instance the formation of blood vessels is important for blood supply to the biological part being produced, so that accelerated vessel-formation comes into questions in terms of addition of an anglogenesis factor as cytokine component of the active ingredient system. Similarly, accelerated formation of nerve connections can be important, and can be realized by a corresponding introduction of additional cytokines into the active substance complex.

It was an object of the present invention to make the active substance complex available for wider use.

This object is achieved by the use of said active substance complex to create an endoprosthesis implant. Compared with the conventionally used endprostheses not having the active substance complex, this permits long-term stabilizing of the endoprosthesis. In this use according to the invention, an active substance complex is used which is suitable for creating biological parts in the form of bones and has the following components which differ from one another and are specifically adapted to creating bone, namely at least one structural component based on extracellular material specifically adapted to the cells of the bone which is to be created, at least one recruiting component, at least one adhesion component, and at least one growth and/or maturation component.

The discovery of this use according to the invention was the result of extensive studies on combining the active substance complex with different support materials, in particular metal support materials. The combination of a support material with the active substance complex is not unproblematic. Based on previous experience of the active substance complex and of its complex mode of action, one would have to expect at least a reduced formation or recreation of the particular biological part to be treated, for example osseous regeneration. The risk of a histotoxic reaction has also been suspected.

The solution to this object was therefore not obvious since, as has already been explained, it is extremely problematic to combine the active substance complex and a support, in this case an endoprosthesis, because the functions of the active substance complex in the bone defect could then be disturbed or at least complicated by possible immune reactions.

The endoprosthesis to be stabilized has an outer surface which is coated at least partially with the active substance complex and/or it has at least one cavity which is filled with the active substance complex.

This coating and/or filling with the active substance complex is intended to permit more rapid and permanent incorporation of the endoprosthesis in the organism. Accelerated and at the same time improved incorporation of the endoprosthesis at the implanted site results in longer-term stability and in greater and earlier loadability of the endoprosthesis.

According to a further embodiment, the endoprosthesis has at least one cavity which is filled with the active substance complex, the active substance complex additionally being applied to a further support material. Collagen or a suitable polymer can be used as such a further support material. The collagens of types I, IV, V and VII are mentioned here in particular. The collagens can be used for example in the form of webs or gels and they in particular have an inherently good immunological compatibility and are easy to process.

The polymer support materials which can be used are in particular polymers of natural monomers, such as polyamino acids (polylysin, polyglutamic acid, etc.), and polymers of lactic acid. Copolymers can also be used, for example of polylactic acid and hydroxyacetic acid.

Polylactates are polyesters of lactic acid having the chemical formula:

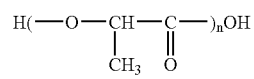

Direct polymerization of the monomers results in polymers with relatively low molecular weights. The upper limit is about 20 000 Da. Higher molecular weights can result by linking of cyclic dimers at high temperature and low pressure and in the presence of catalysts. Lactic acid polymers are biodegradable, biocompatible, insoluble in water, and characterized by a high degree of strength.

The additional use of a further support material such as collagen or the stated polymers reduces the amount of active substance complex needed to completely fill the cavity of the endoprosthesis, without adversely affecting the basic efficiency of the active substance complex. In this way, the use of the active substance complex is made more economically favorable.

The invention also relates to an endoprosthesis which is coated with or which comprises the active substance complex in one of its embodiments according to the use.

Figure 3:
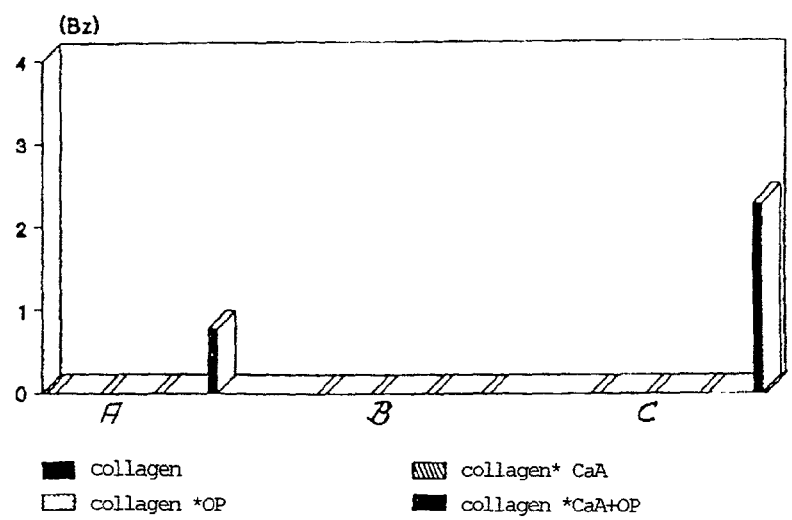
Figures 4A, 4B:
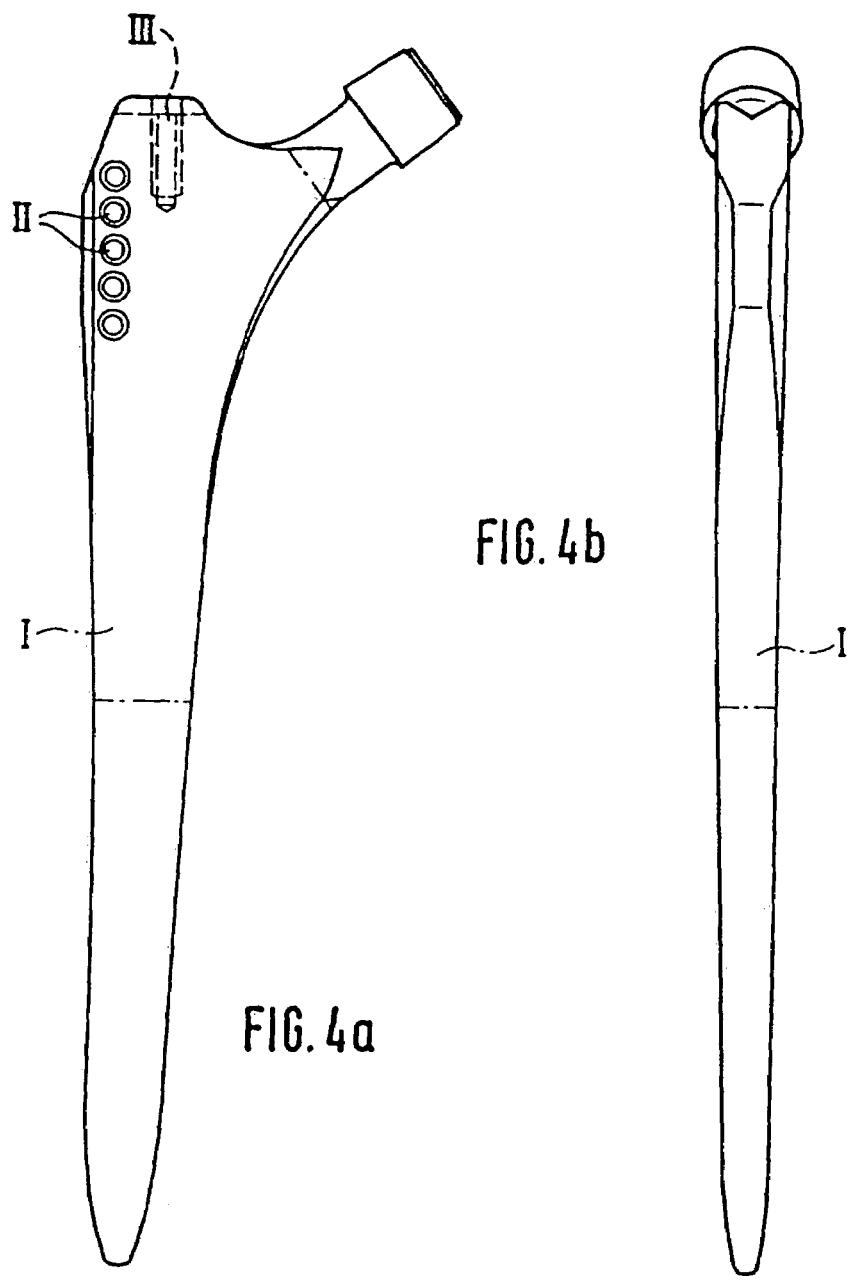

The invention is explained in greater detail below on the basis of examples and with reference to the attached drawing, in which:

FIG. 1 shows a diagrammatic representation of new bone formation in rabbits using the active substance complex, compared with an untreated sample, FIG. 2 shows a diagrammatic representation of new bone formation in sheep using the active substance complex, with tricalcium phosphate as support material, compared with pure tricalcium phosphate, FIG. 3 shows a diagrammatic representation of new bone formation in rats using the active substance complex, with different collagens as support material, compared with pure collagens, FIG. 4a shows a side view of an endoprosthesis used for coating with the active substance complex, and FIG. 4b shows a further side view of the endoprosthesis, turned through 90° compared with FIG. 4a.

I. PREPARATION OF THE ACTIVE SUBSTANCE COMPLEX

The main steps in the preparation of the active substance complex are described below: Tubular bones from calves, sheep, rabbits or rats were cleaned, the bone marrow, inter alia, was removed, and the bones were then frozen. The frozen bone was ground to a particle size of less than 2 mm. The ground bone pieces were defatted in acetone and decalcified in 0.6 N hydrochloric acid. The product was then freeze-dried and a demineralized bone matrix was obtained which was extracted in 4 molar guanidium-HCl solution. The extraction solution was dialyzed against distilled water and the active substance complex was obtained by centrifuging off and freeze-drying in the precipitate.

This basic method of preparation is shown below as a flow chart.

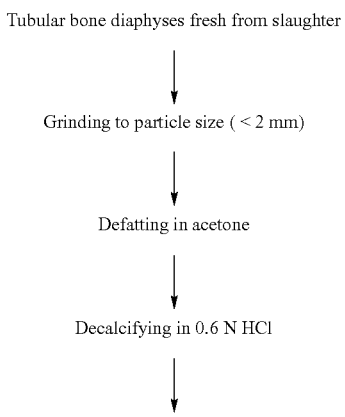

FIG. 1: Flow chart showing preparation of the active substance complex

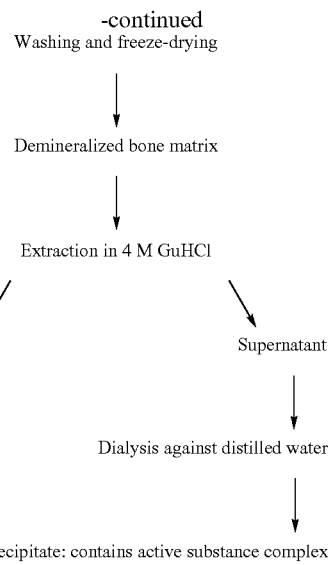

II. Efficacy of the Active Substance Complex Without Use of Support Materials

To show that the active substance complex is effective per se, a test is first set out in which the active substance complex is implanted without additional support materials.

1. Animals Used in the Test

Female chinchilla rabbits with a mean bodyweight of 3089 g were used. They received a rabbit maintenance diet and double-ozonized tap water acidified with hydrochloric acid to pH 4.5 ad libitum.

The animals were anaesthetized by subcutaneous injection of a mixture of ketamine and xylazine.

2. Preparation of a Bone Defect in the Rabbits

An internally cooled drill was used to prepare an implant bed of 4 mm diameter and circa 9 mm depth in the knee joint (distal end of femur) of the rabbit. The bore hole thus formed was then filled in each case with and 90 mg of the active substance complex which had been produced as described under I. A further bore hole in each case was left untreated and served as a control for new bone formation.

FIG. 1 shows the new bone formation in the untreated hole and in the bore hole after implantation of the active substance complex and also the density of the surrounding pre-existing spongy substance 28 days after the operation (n=2/active substance quantity).

Analysis of the tests revealed that the density of the spongy substance surrounding the bore holes after implantation of 30 mg of the active substance complex was 45% higher than in the untreated hole, and, after implantation of 90 mg of the active substance complex, was 69% higher than in the untreated hole. The quantity of pre-existing spongy substance had no influence at all on the regeneration in the defect because the new bone formation after insertion of the active substance complex did not start from the periphery of the bore hole but instead was distributed uniformly across the defect.

III. Bone Formation in the Mandible of Sheep Using Tricalcium Phosphate (TCP)

Tricalcium phosphate (TCP) is a calcium phosphate ceramic based on the CaO/P$_2$O$_5$ system and is prepared by pressing and subsequently sintering the starting materials calcium oxide (CaO) and diphosphorus pentoxide ($P_2O_5$). Alternatively, it can also be prepared in a hot-pressing step.

1. Animals Used for the Tests

Fully grown domestic sheep from Viehzentrale Südwest AG of Stuttgart were used in the tests described below. They were supplied with hay and water and, three days before the operation, a slurry of Altromin pellets.

The animals were premedicated with 1 ml xylazine/1 ml ketanest i.m. The sheep were then anesthetized with Nembutal.

2. Preparation of the Implant

TCP was suspended in a solution of 100 mg of dissolved active substance complex with 10 ml of water and deep-frozen with liquid nitrogen under constant stirring. After 24 hours of freeze-drying and subsequent gas sterilization (ethylene oxide), the TCP thus doped with the active substance complex was introduced into the mandibular defect described below in a sheep. In addition, a further mandibular defect serving for comparison purposes was filled with undoped TCP sterilized in an autoclave.

3. Preparation of the Mandibular Defect in Sheep

A sheep mandible was suitably prepared and, with physiological saline solution as coolant, a trephine of 5 mm diameter was used to cut out and remove in each case a standardized cylinder of bone. One of the bore holes thus formed was then filled with TCP, which had been doped with the active substance complex according to test procedure 1, and the second bore hole was filled with undoped TCP.

For purposes of clarity, the results of the bone growth in the mandibular defects are shown in graph form in FIG. 2. The test duration was 26 days and 41 days respectively.

It was found that doping TCP with the active substance complex accelerated bone regeneration of the mandibular defect in both sheep No. 811 and No. 86 by about 100% in the initial phase. After 41 days, the rate of acceleration of bone regeneration was still 10%. Bone healing is therefore much more rapid, particularly at the start, than it is without the osteoproductive effect of the implants doped with the active substance complex.

This finding is of importance particularly for coating endoprostheses with the active substance complex. An endoprosthesis coated with the active substance complex, for example in the case of a fracture of the neck of the femur, accordingly permits more rapid incorporation of the prosthesis and thus more rapid regeneration and recovery of the respective patient. The length of the hospital stay is therefore shortened.

IV. Tests with Collagens as Support Materials

The already known active substance complex discussed above can be used for the incorporation of endoprostheses. In the production of the active substance complex, the quantitative yield at the required degree of purity is very low. We therefore examined whether there are support materials which can be combined with the active substance complex so as to reduce the quantity of active substance complex needed for the particular objective, but without thereby reducing its bone-forming efficiency.

1. Active Substance Complex

The active substance complex used for the purposes of the tests described below was prepared exactly in the manner described under I., using tubular bones from calves.

2. Animals Used in the Tests

Male Wistar rats weighing between 350 and 400 g were used and were kept in an air-conditioned animal housing at 23° C. and about 50% relative humidity. They were given a maintenance diet for rats and mice.

Two implants of the same support material were introduced into the abdominal musculature of each test animal, of which one implant was coated with the active substance complex while the other remained uncoated and served as a comparison implant. The animals were sacrificed after 21 days, and the affected areas of the implants in the abdominal musculature were explanted and histologically evaluated.

3. Support Materials Used

In these tests, collagen materials were used which are all commercially available. Collagen A was a pure, sterile, native, resorbable bovine skin collagen, free from any foreign additives such as stabilizers or disinfectants.

Collagen B was a purified, freeze-dried, lightly cross-linked sterile and nonpyrogenic bovine skin collagen with weakly antigenic properties. The helical structure of the collagen was preserved.

Collagen C comprised pure, native and resorbable bovine collagen fibrils.

All the collagens used were in web form. Collagen web sections each of 50 mg were cut out, and 1 ml of the active substance complex solution (3 mg/ml) was added in each case. In the control implants, 1 ml of distilled water was added instead. The collagen web sections thus treated were frozen at −20° C., freeze-dried and yielded implants with a diameter of about 10 mm and a thickness of about 5 mm. FIG. 3 shows the bone formation results for collagen implants A, B and C in immunosuppressed animals and non-immunosuppressed animals after 21 days, with and without coating with the active substance complex (cyclosporin A). Here, the evaluation figure (BZ) corresponds to the arithmetic mean of the evaluation figures from three independent persons on six implants of each group.

Collagen A coated with the active substance complex showed a bone formation effect in immunosuppressed animals after this period of time, whereas this could not be demonstrated for collagen B. By contrast, however, collagen C showed a very pronounced bone formation effect.

It follows from this that it depends on the preparation of the particular collagen used and this dictates its suitability as a support material. Collagens which are immunogenic are not suitable for use as support materials.

IV. Testing Support Materials for Their Biocompatibility

In tests relating to the improvement of the long-term stability of endoprostheses, titanium disks of different surface roughness (100, 20 and 0.5 μm), a $TiAl_6V_4$ alloy (0.5 μm) and $Al_2O_3$ disks from the company Friedrichsfeld and hydroxylapatite disks from Feldmühle AG were used. Hydroxylapatite is obtained by ceramic firing of pentacalciumhydroxide triphosphate powder at 1250° C. In addition, a hydroxylapatite ceramic can also be produced using a natural material such as the carbonate skeleton of red alga. After a washing and drying procedure, the organic constituents are first removed by pyrolysis at a temperature of about 700° C. This is followed by conversion to hydroxylapatite by addition of phosphate solution at elevated pressure and increased temperature.

In a further method for producing a hydroxylapatite ceramic, starting from the natural skeleton of corals, the calcium carbonate of the corals is converted by hydrothermal conversion to hydroxylapatite or a mixture of hydroxylapatite and other mineral structures. In the material thus obtained, the coralline structure, i.e. in particular the interconnecting pore system of the coral, is preserved.

The coatings with the active substance complex, which had been prepared using the general procedure set out above, were applied by the dip-coating method. Dip-coating is understood as a coating method in which the object to be coated, in this case the disks, is dipped into a solution with a desired predetermined concentration of the coating agent, in this case the active substance complex. This is followed by freeze-drying. Thin cover layers or coatings are obtained. The testing of the specified materials for their biocompatibility was carried out in particular with reference to the surface roughness (n=20; four disks each).

This biocompatibility testing of the materials under investigation revealed that titanium, with the highest number of living cells and the best ratio of living cells to dead cells, is very well suited as a support material. While hydroxylapatite provided a similarly good result, $TiAl_6V_4$ was considerably poorer.

Generally, as regards surface roughnesses, it was found that the smoothest surfaces, i.e. surfaces with a pore diameter of 0.2–0.5 µm, yielded the best results, with the exception of $TiAl_6V_4$. As the roughness or pore diameter increases, the number of living cells and also the ratio of living cells to dead cells drop. The highest proportion of living (bone) tissue in direct contact with the disk surface was obtained with a pore diameter of about 0.5 µm.

TABLE 1

| Support material | | Number of living cells per cm$^2$ | Number of dead cells per cm$^2$ |
|---|---|---|---|
| Hydroxyl apatite | | | |
| | 0.2–0.5 µm | 1792 ± 700 | 200 ± 37 |
| | 20 µm | 7469 ± 2614 | 2238 ± 715 |
| | 50 µm | 4477 ± 408 | 1692 ± 427 |
| Osprovit (Feldmühle) | | 7930 ± 2007 | 1638 ± 377 |
| Titanium | | | |
| | 0.5 µm | 11377 ± 2538 | 1054 ± 308 |
| | 20 µm | 9600 ± 3038 | 1754 ± 439 |
| | 100 µm | 2308 ± 669 | 2085 ± 623 |
| $TiAl_6V_4$ | 0.5 µm | 7200 ± 1062 | 2800 ± 954 |
| $Al_2O_3$, extra pure, polished | | 11446 ± 1500 | 2292 ± 600 |

The results of these tests could now be carried over to the coating of endoprostheses with the active substance complex. A view of the endoprosthesis used is shown in FIG. 4.

Before the endoprostheses were used, their outer surface (I) was coated with the active substance complex by the dip-coating process, and the active substance complex was additionally introduced into the inner cavities of the prosthesis stem (II) which have openings on the stem surface. This has the advantage, in the event of possible future loosening of the endoprostheses, that the active substance complex can be applied subsequently without any great effort and leads to bone formation and thus to stabilizing of the endoprosthesis. If so desired, a coating with the active substance complex can also be provided in the area of the screw connection (III).

The fact that coating with the active substance complex leads to higher loading capacities compared with uncoated surfaces is illustrated in Table 2, using the example of hydroxylapatite (HA). The tensile strength values at the interface between different implant materials were determined in N/mm$^2$±standard deviation. Hydroxylapatite prepared by hot isostatic pressing (HIP) was compared with hydroxylapatite additionally coated with the active substance complex. The implant material was implanted in the distal area of the femur of rabbits and examined after 84 days. The tensile strength values found are set out in the following table.

TABLE 2

| Material | SR (µm) | Days | n | Tensile strength |
|---|---|---|---|---|
| HA HIP | 0.5 | 84 | 10 | 1.53 ± 0.24 |
| HA HIP AS | 0.5 | 84 | 6 | 2.27 ± 0.31 |

N = number of implants
AS = coating with active substance complex
HIP = hot isostatic pressing
SR = surface roughness Finally, it must be pointed out again that the tests carried out for the purposes of the present invention are all carefully designed model tests, because the actual subject, i.e. the endoprosthesis implanted for example in the area of the femoral bone, could not be made available for the tests, as it would not have been acceptable to conduct these tests on the human body.

In addition, the invention can be applied to all conceivable endoprostheses. The description of the example of the endoprosthesis in the area of the neck of the femur is illustrative in character.

The invention claimed is:

1. An endoprosthesis implant having an outer surface with pores, said pores having a pore diameter of 0.2–0.5 µm which is partially coated with an active substance complex, said active substance complex comprising the following components derived from bone:
    at least one structural component comprising a macromolecular three-dimensional matrix derived from bone-specific proteins;
    at least one recruiting component comprising a chemotactic material for recruiting bone growth cells to said matrix;
    at least one adhesion component for adhering said cells to said matrix; and
    at least one growth or maturation component.

2. The endoprosthesis implant of claim 1, wherein the surface includes at least one cavity which is filled with the active substance complex.

3. An endoprosthesis implant having at least one cavity with an outer surface inside the cavity with a diameter of 0.2–0.5 µm which is filled with an active substance complex, said active substance complex comprising the following components derived from bone:
    at least one structural component comprising a macromolecular three-dimensional matrix derived from bone-specific proteins;
    at least one recruiting component comprising a chemotactic material for recruiting bone growth cells to said matrix;
    at least one adhesion component for adhering said cells to said matrix; and
    at least one growth or maturation component.

4. The endoprosthesis implant of claim 1, wherein the structural component is selected from the group consisting of collagen, elastin or proteoglycans.

5. The endoprosthesis implant of claim 1, wherein the recruiting component is selected from the group consisting of at least one chemotactic peptide or metabolite of arachidonic acid.

6. The endoprosthesis implant of claim 1, wherein the adhesion component is selected from the group consisting of fibronectin, tenascin, laminin collagen types IV, V, VII, L-CAM, N-CAM or integrin.

7. The endoprosthesis implant of claim 1, wherein the growth and maturation component is selected from the group consisting of cytokines.

8. The endoprosthesis implant of claim 1, wherein the active substance complex further comprises a support material selected from the group consisting of non-immunogenic collagen and polymers of natural monomers.

9. The endoprosthesis implant of claim 3, wherein the structural component is selected from the group consisting of collagen, elastin or proteoglycans.

10. The endoprosthesis implant of claim 3, wherein the recruiting component is selected from the group consisting of at least one chemotactic peptide or metabolite of arachidonic acid.

11. The endoprosthesis implant of claim 3, wherein the adhesion component is selected from the group consisting of fibronectin, tenascin, laminin, collagen types IV, V, VII, L-CAM, N-CAM or integrin.

12. The endoprosthesis implant of claim 3, wherein the growth and maturation component is selected form the group consisting of cytokines.

13. The endoprosthesis implant of claim 3, wherein the active substance complex further comprises a support material selected from the group consisting of non-immunogenic collagen and polymers of natural monomers.

* * * * *